United States Patent [19]

Karanewsky et al.

[11] Patent Number: 5,650,408

[45] Date of Patent: Jul. 22, 1997

[54] THIAZOLO BENZAZEPINE CONTAINING DUAL ACTION INHIBITORS

[76] Inventors: Donald S. Karanewsky, 1797 Continental La., Escondido, Calif. 92029; Chong-Qing Sun, 527 Dutch Neck Rd., East Windsor, N.J. 08520

[21] Appl. No.: 481,976

[22] Filed: Jun. 7, 1995

[51] Int. Cl.$^6$ .......................... A61K 31/55; C07D 513/04
[52] U.S. Cl. .......................... 514/214; 540/521
[58] Field of Search .................... 540/521; 514/214

[56] References Cited

U.S. PATENT DOCUMENTS

| | | |
|---|---|---|
| 3,856,798 | 12/1974 | Meyer et al. ............... 260/294.8 |
| 4,105,776 | 8/1978 | Ondetti et al. ............... 424/274 |
| 4,186,200 | 1/1980 | Kubo et al. ............... 424/256 |
| 4,192,945 | 3/1980 | Ondetti ............... 546/245 |
| 4,225,495 | 9/1980 | Ondetti ............... 260/244.4 |
| 4,337,201 | 6/1982 | Petrillo, Jr. ............... 548/413 |
| 4,339,600 | 7/1982 | Ondetti et al. ............... 562/426 |
| 4,374,829 | 2/1983 | Harris et al. ............... 424/177 |
| 4,409,146 | 10/1983 | Thorsett et al. ............... 260/239.3 |
| 4,410,520 | 10/1983 | Watthey ............... 424/244 |
| 4,415,496 | 11/1983 | Harris et al. ............... 260/239.3 |
| 4,432,971 | 2/1984 | Karanewsky et al. ............... 424/177 |
| 4,432,972 | 2/1984 | Karanewsky et al. ............... 424/177 |
| 4,460,579 | 7/1984 | Karanewsky ............... 424/200 |
| 4,465,679 | 8/1984 | Huang et al. ............... 424/244 |
| 4,470,988 | 9/1984 | Watthey ............... 424/263 |
| 4,473,575 | 9/1984 | Watthey ............... 424/263 |
| 4,477,464 | 10/1984 | Slade et al. ............... 424/275 |
| 4,512,924 | 4/1985 | Attwood et al. ............... 260/243.3 |
| 4,537,885 | 8/1985 | Watthey ............... 514/183 |
| 4,539,150 | 9/1985 | Katakami et al. ............... 260/239.3 |
| 4,548,932 | 10/1985 | Sugihara et al. ............... 514/211 |
| 4,575,503 | 3/1986 | Watthey ............... 514/213 |
| 4,584,294 | 4/1986 | Ruyle ............... 514/214 |
| 4,587,050 | 5/1986 | Harris et al. ............... 260/239.3 |
| 4,587,238 | 5/1986 | Harris et al. ............... 514/183 |
| 4,594,341 | 6/1986 | Cheung et al. ............... 514/211 |
| 4,617,301 | 10/1986 | Patchett et al. ............... 514/214 |
| 4,629,787 | 12/1986 | Harris et al. ............... 540/528 |
| 4,680,392 | 7/1987 | Harris et al. ............... 540/527 |
| 4,699,905 | 10/1987 | Yanagisawa et al. ............... 514/211 |
| 4,711,884 | 12/1987 | Karanewsky ............... 514/226 |
| 4,722,810 | 2/1988 | Delaney et al. ............... 260/402.5 |
| 4,734,410 | 3/1988 | Yanagisawa et al. ............... 514/212 |
| 4,749,688 | 6/1988 | Haslanger et al. ............... 514/19 |
| 4,801,609 | 1/1989 | Haslanger et al. ............... 514/506 |
| 4,824,832 | 4/1989 | Flynn et al. ............... 514/214 |
| 4,873,235 | 10/1989 | Parsons et al. ............... 514/312 |
| 4,879,309 | 11/1989 | Doll et al. ............... 514/513 |
| 4,963,539 | 10/1990 | Delaney ............... 514/119 |
| 4,973,585 | 11/1990 | Flynn et al. ............... 514/214 |
| 5,061,710 | 10/1991 | Haslanger et al. ............... 514/266 |
| 5,075,302 | 12/1991 | Neustadt ............... 514/211 |
| 5,098,934 | 3/1992 | Vevert et al. ............... 514/513 |
| 5,190,974 | 3/1993 | Clemence et al. ............... 514/513 |
| 5,208,236 | 5/1993 | Neustadt ............... 514/237.5 |
| 5,223,516 | 6/1993 | Delaney et al. ............... 514/339 |
| 5,225,401 | 7/1993 | Seymour ............... 519/19 |
| 5,232,920 | 8/1993 | Neustadt ............... 514/212 |
| 5,238,924 | 8/1993 | Smith ............... 514/19 |
| 5,262,436 | 11/1993 | Haslanger et al. ............... 514/513 |
| 5,362,727 | 11/1994 | Robl ............... 514/214 |
| 5,366,973 | 11/1994 | Flynn et al. ............... 514/221 |
| 5,504,080 | 4/1996 | Karanewsky ............... 514/214 |
| 5,508,272 | 4/1996 | Robl ............... 514/80 |
| 5,525,723 | 6/1996 | Robl ............... 540/521 |

FOREIGN PATENT DOCUMENTS

| | | | |
|---|---|---|---|
| 249223 | 12/1987 | European Pat. Off. ............... | 540/520 |
| 249224 | 12/1987 | European Pat. Off. ............... | 540/520 |
| 481522 | 4/1992 | European Pat. Off. ............... | 540/521 |
| 524553 | 1/1993 | European Pat. Off. ....... | A61K 37/64 |
| 534363 | 3/1993 | European Pat. Off. ............... | 540/521 |
| 534396 | 3/1993 | European Pat. Off. ............... | 540/521 |
| 534492 | 3/1993 | European Pat. Off. ............... | 540/521 |
| 595610 | 5/1994 | European Pat. Off. ............... | 540/520 |
| 599444 | 6/1994 | European Pat. Off. ............... | 540/52 |
| 629627 | 12/1994 | European Pat. Off. ............... | 540/521 |
| 2207351 | 2/1989 | United Kingdom ........... | A61K 31/66 |
| WO93/16103 | 8/1993 | WIPO ............... | 540/521 |
| WO94/10193 | 5/1994 | WIPO ............... | 540/521 |
| WO94/26719 | 11/1994 | WIPO ............... | A61K 31/55 |
| WO94/28901 | 12/1994 | WIPO ............... | A61K 31/55 |

OTHER PUBLICATIONS

Adams et al., Synthetic Communications, vol. 18, 2225–2231 (1988).

Attwood et al., FEBS Letters, vol. 165, pp. 201–206 (1984).

Attwood et al., J. Chem. Soc. Perkin Trans I (1986) pp. 1011–1019.

(List continued on next page.)

*Primary Examiner*—Robert T. Bond

[57] ABSTRACT

Compounds of the formula

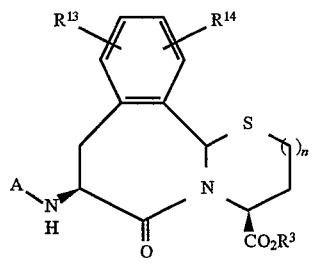

wherein A is

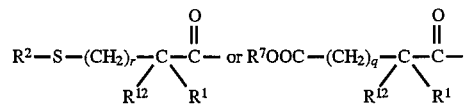

are dual inhibitors of NEP and ACE. Compounds wherein A is

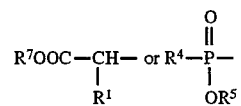

are selective ACE inhibitors.

14 Claims, No Drawings

OTHER PUBLICATIONS

Bolos et al., J. Org. Chem., 57, 3535–3539 (1992).
Bolos et al., Tetrahedron, vol. 48, pp. 9567–9576 (1992).
Boyer, T. D. "Cirrhosis of the Liver and Its Major Sequelae" in: Wyngaarden, J. B. et al., Cecil Textbook of Medicine, vol. 1 (Saunders Co., 1992) pp. 786–789.
Chackalamannil et al., Bioorganic & Medicinal Chemistry Letters, vol. 2, pp. 1003–1006 (1992).
Das et al., Bioorganic & Medicinal Chemistry Letters, vol. 4, pp. 2193–2198 (1994).
Delaney et al., Bioorganic & Medicinal Chemistry Letters, vol. 4, pp. 1783–1788 (1994).
Dussaule et al., Jour. of Clinical Endocrinology and Metabolism, vol. 72, pp. 653–659 (1991).
Fernandez–Cruz, The Lancet, Dec. 21/28, pp. 1439–1440 (1985).
Flynn et al., J. Med. Chem., 36, pp. 2420–2423 (1993).
Flynn, Tetrahedron Letters, vol. 31, pp. 815–818 (1990).
Fobian et al., 206th Meeting of the Amer. Chem. Society, Aug. 1993 Abstr. ORG 297.
Fyhrquist et al., The Lancet, Dec. 21/28, p. 1439 (1985).
Hanau et al., 206th Meeting of the Amer. Chem. Society, Aug. 1993 Abstr. ORG 298.
Itoh et al., Chem. Pharm. Bull., vol. 34, pp. 1128–1147 (1986).
Itoh et al., Chem. Pharm. Bull., vol. 34, pp. 2078–2089 (1986).
Laffi et al., Gastroenterology, vol. 96, pp. 167–177 (1989).
Moeller et al., Tetrahedron Letters, vol. 33, pp. 6041–6044 (1992).
Naming and Indexing of Chemical Substances for Chemical Abstracts, 1987 Index Guide, Section 203.
Natoff et al., Drugs Of the Future, vol. 12, pp. 475–483 (1987).
Parsons et al., Biochem and Biophysical Research Comm. 117, pp. 108–113 (1983).
Robl et al., Bioorganic & Medicinal Chem. Letters, vol. 4, pp. 1795–1800 (1994).
Robl et al., Bioorganic & Medicinal Chemistry Letters, vol. 4, pp. 1789–1794 (1994).
Robl et al., Bioorganic & Medicinal Chemistry Letters, vol. 4, pp. 2055–2060 (1994).
Robl et al., J. Am. Chem. Soc., 116, pp. 2348–2355 (1994).
Robl, Tetrahedron Letters, vol. 35, pp. 393–396 (1994).
Robl, Tetrahedron Letters, vol. 35, pp. 1393–1396 (1994).
Slade et al., J. Med. Chem., 28, pp. 1517–1521 (1985).
Smith et al., Biochemistry, vol. 14, pp. 766–771 (1975).
Thorsett et al., J. Med. Chem., 29, pp. 251–260 (1986).
Thorsett, Actual Chim. Ther., vol. 13, pp. 257–268 (1986).
Watthey et al., J. Med. Chem., 28, pp. 1511–1516 (1985).
Yanagisawa et al., J. Med. Chem., 30, pp. 1984–1991 (1987).
Yanagisawa et al., J. Med. Chem., 31, pp. 422–428 (1988).

THIAZOLO BENZAZEPINE CONTAINING DUAL ACTION INHIBITORS

BACKGROUND OF THE INVENTION

Captopril, (S)-1-(3-mercapto-2-methyl-1-oxopropyl)-L-proline, having the structural formula

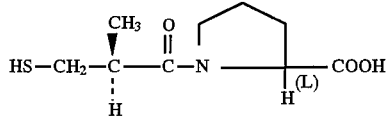

is an orally active angiotension converting enzyme inhibitor useful for treating hypertension and congestive heart failure. See Ondetti et al. U.S. Pat. No. 4,105,776.

Enalapril, (S)-1-[N-[1-(ethoxycarbonyl)-3-phenylpropyl]-L-alanyl]-L-proline, having the structural formula

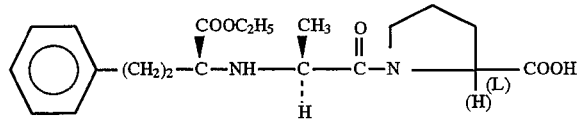

is also an orally active angiotensin converting enzyme inhibitor. Enalapril contains the L-alanyl-L-proline dipeptide. A related compound, lisinopril, also possesses oral angiotensin converting enzyme inhibitor activity and contains the L-lysyl-L-proline dipeptide. See Harris et al. U.S. Pat. No. 4,374,829.

Fosinopril sodium, (4S)-4-cyclohexyl-1-[[(R)-[(S)-1-hydroxy-2-methylpropoxy](4-phenylbutyl)-phosphinyl]acetyl]-L-proline propionate (ester), sodium salt having the structural formula

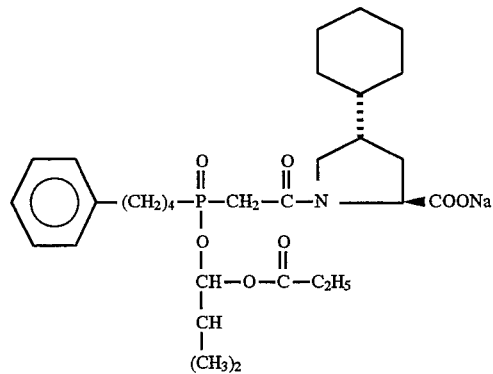

is also an orally active angiotensin converting enzyme inhibitor useful for treating hypertension. See Petrillo U.S. Pat. No. 4,337,201.

Haslanger et al., in U.S. Pat. No. 4,749,688, disclose treating hypertension by administering neutral metalloendopeptidase inhibitors alone or in combination with atrial peptides or angiotensin converting enzyme inhibitors.

Neustadt, in U.S. Pat. No. 5,075,302, discloses that mercaptoacyl amino lactams of the formula

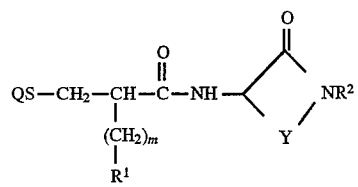

wherein Y includes propylene and butylene, $R^1$ is lower alkyl, aryl or heteroaryl, and $R^2$ is hydrogen, lower alkyl, lower alkoxy lower alkyl, aryl-lower alkyl or heteroaryl-lower alkyl are endopeptidase inhibitors. Neustadt discloses employing such compounds alone or in combination with angiotensin converting enzyme inhibitors to treat cardiovascular diseases such as hypertension, congestive heart failure, edema and renal insufficiency.

Delaney et al., in U.K. Patent 2,207,351, disclose that endopeptidase inhibitors produce diuresis and natriuresis and are useful alone or in combination with angiotensin converting enzyme inhibitors for the reduction of blood pressure. Delaney et al. include various mercapto and acylmercapto amino acids and dipeptides among their endopeptidase inhibiting compounds.

Flynn et al., in European Patent Application 481,522, disclose dual inhibitors of enkephalinase and angiotensin converting enzyme of the formulas

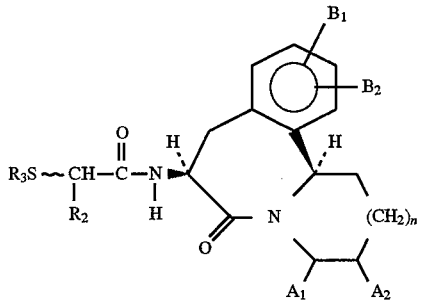

and

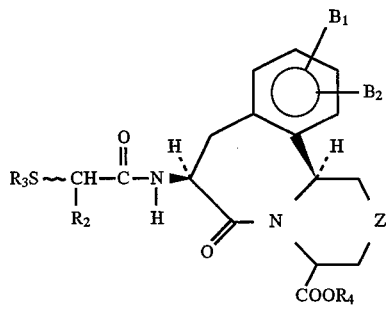

wherein n is zero or one and Z is O, S, —$NR_6$— or

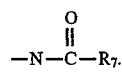

Additional tricyclic dual inhibitors are disclosed by Warshawsky et al. in European Patent Applications 534,363, 534,396 and 534,492.

Karanewsky et al., in U.S. Pat. Nos. 4,432,971 and 4,432,972, disclose phosphonamidate angiotensin converting enzyme inhibitors of the formula $$\begin{array}{c} \text{O} \quad R_1 \quad R_2 \quad \text{O} \\ \| \quad | \quad | \quad \| \\ R_{21}-P-N-CH-C-X \\ | \\ OR_3 \end{array}$$

wherein X is a substituted imino or amino acid or ester.

Karanewsky, in U.S. Pat. No. 4,460,579, discloses angiotensin converting enzyme inhibitors including those of the formula $$\begin{array}{c} \text{O} \quad\quad\quad R_1 \quad \text{O} \\ \| \quad\quad\quad | \quad \| \\ R_7-P-NH-X-CH-C-OR_2 \\ | \\ OR_8 \end{array}$$

and, in U.S. Pat. No. 4,711,884, discloses angiotensin converting enzyme inhibitors including those of the formula $$\begin{array}{c} \text{O} \quad\quad\quad R_1 \quad \text{O} \\ \| \quad\quad\quad | \quad \| \\ R_3-C-CH-NH-X-CH-C-OR_2 \\ | \\ R_4 \end{array}$$

wherein X is a thiazine or thiazepine.

SUMMARY OF THE INVENTION

This invention is directed to novel compounds containing a thiazolo benzazepine which are useful as angiotensin converting enzyme inhibitors. Some of these compounds possess neutral endopeptidase inhibitory activity as well. This invention is also directed to pharmaceutical compositions containing such selective or dual action inhibitors and to methods of using such compositions.

The novel thiazolo benzazepine inhibitors of this invention include those compounds of the formula (I)

[Structure of formula (I) with R$^{13}$, R$^{14}$ on aromatic ring, A-NH group, S, N, (CH$_2$)$_n$, CO$_2$R$^3$]

and pharmaceutically acceptable salts thereof wherein:

$$\text{A is } R^2-S-(CH_2)_r-\underset{R^{12}}{\overset{R^1}{C}}-\overset{O}{\overset{\|}{C}}-, \quad R^7OOC-(CH_2)_q-\underset{R^{12}}{\overset{R^1}{C}}-\overset{O}{\overset{\|}{C}}-,$$

$$R^7OOC-\underset{R^1}{\overset{}{CH}}- \text{ or } R^4-\underset{OR^5}{\overset{O}{\overset{\|}{P}}}-;$$

$R^1$ and $R^{12}$ are independently selected from hydrogen, alkyl, alkenyl, cycloalkyl, substituted alkyl, substituted alkenyl, aryl, substituted aryl, heteroaryl, cycloalkyl-alkylene-, aryl-alkylene-, substituted aryl-alkylene- and heteroaryl-alkylene-, or $R^1$ and $R^{12}$ taken together with the carbon atom to which they are attached, complete a cycloalkyl ring or a benzofused cycloalkyl ring;

$R^2$ is hydrogen, $$\overset{O}{\overset{\|}{R^6-C-}}$$

or $R^{11}$—S—;

$R^3$, $R^5$ and $R^7$ are independently selected from hydrogen, alkyl, substituted alkyl, aryl-(CH$_2$)$_p$—, substituted aryl-(CH$_2$)$_p$—, heteroaryl-(CH$_2$)$_p$—, $$-\underset{R^8}{\overset{}{CH}}-O-\overset{O}{\overset{\|}{C}}-R^9 \quad \text{and} \quad -CH_2-\overset{O\diagdown\!\!\!\diagup O}{\underset{R^{10}}{=\!\!\!\!<}};$$

$R^4$ is alkyl, cycloalkyl-(CH$_2$)$_p$—, substituted alkyl, aryl-(CH$_2$)$_p$—, substituted aryl-(CH$_2$)$_p$— or heteroaryl-(CH$_2$)$_p$—;

$R^6$ is alkyl, substituted alkyl, cycloalkyl-(CH$_2$)$_p$—, aryl-(CH$_2$)$_p$—, substituted aryl-(CH$_2$)$_p$— or heteroaryl-(CH$_2$)$_p$—;

$R^8$ is hydrogen, lower alkyl, cycloalkyl or phenyl;

$R^9$ is hydrogen, lower alkyl, lower alkoxy or phenyl;

$R^{10}$ is lower alkyl or aryl-(CH$_2$)$_p$—;

$R^{11}$ is hydrogen, alkyl, substituted alkyl, cycloalkyl-(CH$_2$)$_p$—, aryl-(CH$_2$)$_p$—, substituted aryl-(CH$_2$)$_p$— or heteroaryl-(CH$_2$)$_p$—, or —S—R$^{11}$ completes a symmetrical disulfide wherein $R^{11}$ is

[Structure with R$^{13}$, R$^{14}$ on aromatic ring, (CH$_2$)$_r$-C-C-N, R$^{12}$, R$^1$, H, S, N, (CH$_2$)$_n$, CO$_2$R$^3$]

$R^{13}$ and $R^{14}$ are each independently selected from hydrogen, alkyl, substituted alkyl, aryl, substituted aryl, halogen, alkoxy and aryl-alkylene, or $R^{13}$ and $R^{14}$ taken together with the carbon atoms to which they are attached complete a six-membered aromatic ring;

n is zero or one;

p is zero or an integer from 1 to 6;

q is zero or an integer from 1 to 3; and r is zero or one.

DETAILED DESCRIPTION OF THE INVENTION

Listed below are definitions of terms used in this specification. These definitions apply to the terms as used throughout this specification, individually or as part of another group, unless otherwise limited in specific instances.

The term "alkyl" refers to straight or branched chain radicals having up to seven carbon atoms. The term "lower alkyl" refers to straight or branched radicals having up to four carbon atoms and is a preferred subgrouping for the term alkyl.

The term "substituted alkyl" refers to such straight or branched chain radicals of 1 to 7 carbons wherein one or more, preferably one, two or three, hydrogens have been replaced by a hydroxy, amino, cyano, halo, trifluoromethyl, —NH(lower alkyl), —N(lower alkyl)$_2$, lower alkoxy, lower alkylthio, or carboxy.

The terms "lower alkoxy" and "lower alkylthio" refer to such lower alkyl groups as defined above attached to an oxygen or sulfur atom, respectively.

The term "cycloalkyl" refers to saturated rings of 3 to 7 carbon atoms with cyclopropyl, cyclobutyl, cyclopentyl and cyclohexyl being most preferred.

The term "alkenyl" refers to straight or branched chain radicals of 3 to 7 carbon atoms having one or two double bonds. Preferred "alkenyl" groups are straight chain radicals of 3 to 5 carbon atoms having one double bond.

The term "substituted alkenyl" refers to such straight or branched radicals of 3 to 7 carbon atoms having one or two double bonds wherein a hydrogen has been replaced by a hydroxy, amino, halo, trifluoromethyl, cyano, —NH(lower alkyl), —N(lower alkyl)$_2$, lower alkoxy, lower alkylthio or carboxy.

The term "alkylene" refers to straight or branched chain radicals having up to seven carbon atoms, i.e., —CH$_2$—, —(CH$_2$)$_2$—, —(CH$_2$)$_3$—, —(CH$_2$)$_4$—,

—CH$_2$—CH—,   —CH—,
       |              |
       CH$_3$        CH$_3$ etc.

The term "aryl" refers to phenyl, 1-naphthyl, and 2-naphthyl. The term "substituted aryl" refers to phenyl, 1-naphthyl and 2-naphthyl having a substituent selected from lower alkyl, lower alkoxy, lower alkylthio, halo, hydroxy, trifluoromethyl, amino, —NH(lower alkyl) or —N(lower alkyl)$_2$, and di- and tri-substituted phenyl, 1-naphthyl or 2-naphthyl wherein said substituents are selected from methyl, methoxy, methylthio, halo, hydroxy and amino.

The term "heteroaryl" refers to unsaturated rings of 5 or 6 atoms containing one or two O and/or S atoms, and/or one to four N atoms, provided that the total number of heteroatoms in the ring is 4 or less. The heteroaryl ring is attached by way of an available carbon or nitrogen atom. Preferred heteroaryl groups include 2-, 3- or 4-pyridyl, 4-imidazolyl, 4-thiazolyl, 2- and 3-thienyl and 2- and 3-furyl. The term heteroaryl also includes bicyclic rings wherein the five or six membered ring containing O, S and/or N atoms as defined above is fused to a benzene or pyridyl ring. Preferred bicyclic rings are 2- and 3-indolyl and 4- and 5-quinolinyl. The mono or bicyclic heteroaryl ring can also be additionally substituted at an available carbon atom by a lower alkyl, halo, hydroxy, benzyl or cyclohexylmethyl. Also, if the mono or bicyclic ring has an available N atom, such N atom can also be substituted by an N-protecting group such as

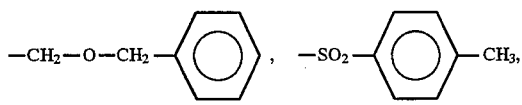

2,4-dinitrophenyl, lower alkyl, benzyl or benzhydryl.

The term "halo" refers to fluorine, chlorine, bromine and iodine.

The compounds of formula I wherein A is

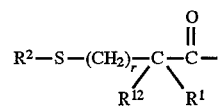

and R$^2$ is hydrogen can be prepared by the general route as shown below in Scheme 1:

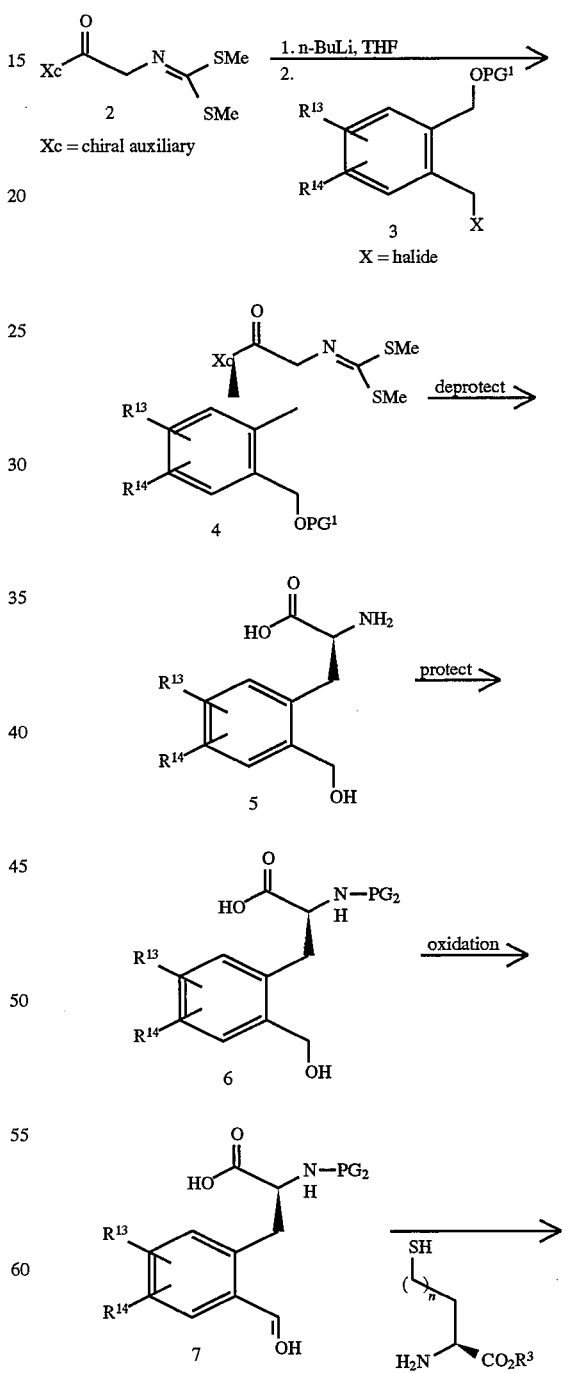

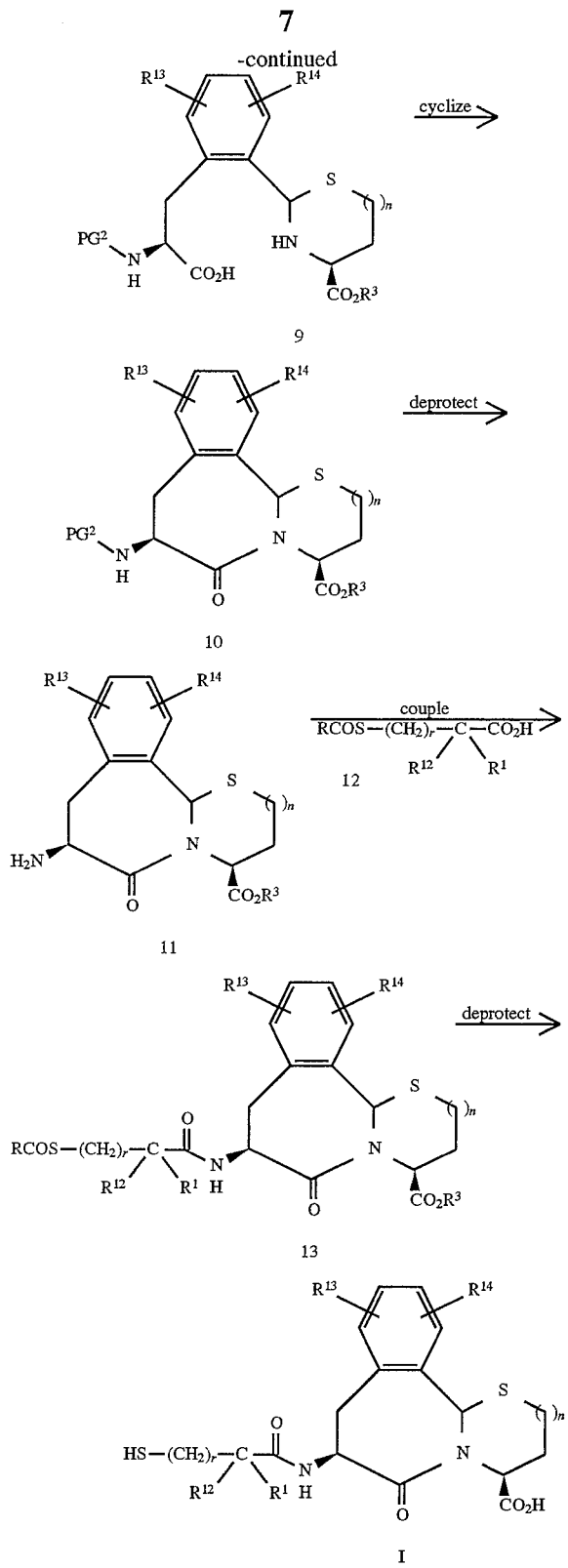

Nitrogen protection of amino acid 5 (preferably with a phthaloyl group, PG²) followed by oxidation affords aldehyde 7. Condensation of aldehyde 7 with a cysteine derivative (where n=0) or a homocysteine derivative (where n=1) gives a compound of formula 9. Cyclization of 9 (with 2-ethoxy-1-ethoxycarbonyl-1,2-dihydroquinoline in tetrahydrofuran) provides a tricyclic compound of formula 10. Selective deprotection of a compound of formula 10 (with hydrazine and methanol for PG² as a phthaloyl group, for example) gives amine 11. Coupling of amine 11 to acid 12 (with benzotriazol-1-yloxytris(dimethylamino) phosphonium hexafluorophosphate (BOP reagent), triethylamine and dichloromethane) gives a compound of the formula 13. Deprotection of a compound of formula 13 affords a compound of formula I.

Compounds of formula I wherein R³ is other than hydrogen can be prepared by reacting intermediate 13 in a suitable solvent or solvent mixture, such as acetonitrile and methanol, with mercuric trifluoroacetate at room temperature. Upon complete disappearance of the starting material, the reaction mixture is treated briefly with gaseous hydrogen sulfide and filtered to remove the black precipitate of mercuric sulfide. The desired product is isolated by the usual means.

The products of formula I from Scheme 1, wherein R² is hydrogen, can be acylated with an acyl halide of the formula

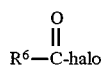

wherein halo is F, Cl or Br, or acylated with an anhydride of the formula

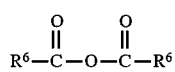

to give other products of formula I wherein R² is

The products of formula I wherein R² is —S—R¹¹, and R¹¹ is alkyl, substituted alkyl, cycloalkyl-$(CH_2)_p$—, aryl-$(CH_2)_p$—, substituted aryl-$(CH_2)_p$— or heteroaryl-$(CH_2)_p$—, can be prepared by reacting the products of formula I from Scheme 1, wherein R₂ is hydrogen, with a sulfonyl compound of the formula

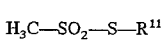

in an aqueous alcohol solvent to yield the desired products. The sulfonyl compounds of the formula $H_3C—SO_2—S—R^{11}$ are known in the literature or can be prepared by known methods. See, for example, Smith et al., Biochemistry, 14, p 766–771 (1975).

The products of formula I wherein R² is SH can be prepared by reacting the product of formula I from Scheme 1, wherein R² is hydrogen, with a sulfonyl compound of the formula $H_3C—SO_2—S—R^{11}$ wherein R¹¹ is triphenylmethyl or trialkylsilyl, followed by removal of the triphenylmethyl or trialkylsilyl group under acidic conditions.

The symmetrical disulfide products of formula I can be prepared by direct oxidation of the product of formula I from Scheme 1, wherein R² is hydrogen, with iodine according to known procedures. See, for example, Ondetti et al. U.S. Pat. No. 4,105,776.

As can be seen in Scheme I, asymmetric alkylation of a glycine derivative 2 with a suitably protected halide 3 (where X is preferably Br or I; and PG¹ is preferably silyl or an acid labile protecting group) provides a compound of formula 4. Compounds of type 2 and 3 may be derived from methods known in the literature. Deprotection of a compound of formula 4 (with 1N aqueous hydrochloric acid, and 2N aqueous lithium hydroxide) provides amino acid 5.

The acylmercapto sidechain compounds 12 wherein $R^{12}$ is hydrogen are described in the literature. See, for example, Ondetti et al. U.S. Pat. Nos. 4,105,776 and 4,339,600, Haslanger et al. U.S. Pat. No. 4,801,609, Delaney et al. U.S. Pat. No. 4,722,810, etc.

The acylmercapto sidechain compounds 12 wherein $R^1$ and $R^{12}$ are both other than hydrogen and r is zero can be prepared by reacting the substituted carboxylic acid of the formula $$\underset{R^{12}}{\overset{}{\diagup}} \underset{R^1}{\overset{}{\diagdown}} HC - \overset{O}{\underset{\|}{C}} - OH$$

with bis[(4-methoxy)phenyl]methyldisulfide in the presence of lithium diisopropylamide to give the compound of the formula $$H_3CO - \langle \bigcirc \rangle - H_2C - S - \underset{R^{12}}{\overset{}{\diagup}} \underset{R^1}{\overset{}{\diagdown}} C - \overset{O}{\underset{\|}{C}} - OH.$$

Treatment of this compound with strong acid such as trifluoromethanesulfonic acid removes the methoxybenzyl protecting group and is followed by acylation with the acyl halide of the formula $$R^6 - \overset{O}{\underset{\|}{C}} - \text{halo}$$

(above) or the anhydride of the formula $$R^6 - \overset{O}{\underset{\|}{C}} - O - \overset{O}{\underset{\|}{C}} - R^6$$

(above) to give compound 12 wherein $R^1$ and $R^{12}$ are both other than hydrogen and r is zero.

Alternatively, the substituted carboxylic acid of the formula $$\underset{R^{12}}{\overset{}{\diagup}} \underset{R^1}{\overset{}{\diagdown}} HC - \overset{O}{\underset{\|}{C}} - OH$$

(above) can be reacted with lithium diisopropylamide and sulfur to give the mercaptan of the formula $$\underset{R^{12}}{\overset{}{\diagup}} \underset{R^1}{\overset{}{\diagdown}} HS - C - \overset{O}{\underset{\|}{C}} - OH.$$

This mercaptan can then be acylated with the acyl halide of the formula $$R^6 - \overset{O}{\underset{\|}{C}} - \text{halo}$$

(above) or the anhydride of the formula $$R^6 - \overset{O}{\underset{\|}{C}} - O - \overset{O}{\underset{\|}{C}} - R^6$$

(above) to give compound 10 wherein $R^1$ and $R^{12}$ are both other than hydrogen and r is zero.

The acylmercapto sidechain compound 12 wherein $R^1$ and $R^{12}$ are both other than hydrogen and r is one can be prepared by reacting the substituted carboxylic acid of the formula $$HO - CH_2 - \underset{R^{12}}{\overset{}{\diagup}} \underset{R^1}{\overset{}{\diagdown}} C - \overset{O}{\underset{\|}{C}} - OH$$

with para-toluenesulfonyl chloride in pyridine to give the lactone of the formula $$\text{(lactone structure with } R^1 \text{ and } R^{12} \text{)}$$

Treatment of this lactone with a cesium thioacid of the formula $$Cs - S - \overset{O}{\underset{\|}{C}} - R^6$$

in the presence of dimethylformamide yields the desired acylmercapto sidechain of compound 12 wherein $R^1$ and $R^{12}$ are both other than hydrogen and r is one.

Compounds of formula I wherein A is $$R^7OOC - \underset{R^1}{\overset{}{\underset{|}{CH}}} - \quad \text{or} \quad R^4 - \underset{OR^5}{\overset{O}{\underset{|}{\overset{\|}{P}}}} -;$$

may be prepared from the corresponding amine 11 above using chemistry described in the literature as known to those skilled in the art.

Compounds of formula I wherein A is $$R^7OOC - (CH_2)_q - \underset{R^{12}}{\overset{}{\diagup}} \underset{R^1}{\overset{}{\diagdown}} C - \overset{O}{\underset{\|}{C}} -$$

can be prepared by coupling the acid of the formula $$R^7OOC - (CH_2)_q - \underset{R^{12}}{\overset{}{\diagup}} \underset{R^1}{\overset{}{\diagdown}} C - \overset{O}{\underset{\|}{C}} - OH \qquad 14$$

wherein $R^7$ is an acid protecting group with the amine 11 in the presence of a coupling reagent such as defined above. Alternatively, the acid of formula 14 can be converted to an activated form such as an acid chloride prior to the coupling reaction.

The acids of formula 14 are described by Warshawsky et al. in European Patent Application 534,396 and 534,492.

While the optically pure form of the compounds of formula I described above is preferred, all forms of the compounds are within the scope of this invention. The above described processes can utilize racemates, enantiomers, or diastereomers as starting materials. When diastereomeric compounds are prepared, they can be separated by conventional chromatographic or fractional crystallization methods.

The compounds of formula I where possible can be isolated in the form of a pharmaceutically acceptable salt. Suitable salts for this purpose are alkali metal salts such as sodium and potassium, alkaline earth metal salts such as calcium and magnesium, salts derived from amino acids such as arginine, lysine, etc., and salts derived from amines such as alkyl amines, e.g., t-butylamine, t-amylamine, etc., substituted alkylamines, e.g., benzylamine, dialkylamines, substituted dialkylamines, e.g., N-methyl glucamine, trialkylamines, substituted trialkylamines and quaternary ammonium salts. These salts can be obtained by reacting the acid form of the compound with a base supplying the desired ion in a medium in which the salt precipitates or in aqueous medium and then lyophilizing.

Preferred compounds of this invention are those wherein:
A is

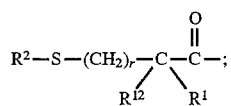

and n is zero. Most preferred is the compound wherein:

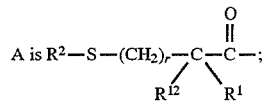

$R^1$, $R^2$, $R^3$, $R^{13}$ and $R^{14}$ are each hydrogen;
$R^{12}$ is benzyl;
n is zero; and
r is zero.
The compounds of formula I wherein A is

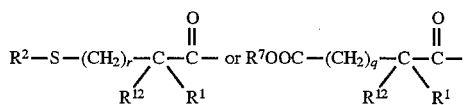

are dual inhibitors possessing the ability to inhibit angiotensin converting enzyme and neutral endopeptidase. The compounds of formula I wherein A is

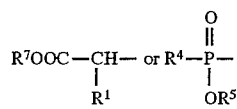

are selective inhibitors possessing the ability to inhibit the angiotensin converting enzyme. Thus, the compounds of formula I, including their pharmaceutically acceptable salts, are useful in the treatment of physiological conditions in which angiotensin converting enzyme inhibitors have been shown to be useful. Such conditions include disease states characterized by abnormalities in blood pressure, intraocular pressure and renin including cardiovascular diseases particularly hypertension and congestive heart failure, glaucoma and renal diseases such as renal failure, diabetic nephropathy and renal impairment following treatment with cyclosporine or other immunosuppressants. Other conditions in which angiotensin converting enzyme inhibitors have been reported to be useful include hepatic cirrhosis, inhibiting the progression of atherosclerosis, preventing or treating hypertensive or diabetic retinopathy, improving myocardial dysfunction during or following a myocardial infarction and preventing restinosis after angioplasty. The dual inhibitors are also useful in the treatment of physiological conditions in which neutral endopeptidase inhibitors have been shown to be useful. Such conditions also include cardiovascular diseases particularly hypertension, hyperaldosteronemia, renal diseases and glaucoma, as well as the relief of acute or chronic pain. Thus, the compounds of formula I are useful in reducing blood pressure and the dual inhibitors of formula I are additionally useful for this purpose due to their diuresis and natriuresis properties. The dual inhibitors are particularly useful in the treatment of congestive heart failure.

The compounds of formula I, including pharmaceutically acceptable salts thereof, can be administered for these effects in amounts similar to those employed previously for angiotensin converting enzyme inhibitors. For example, the compounds of formula I can be administered to a mammalian host such as man at from about 0.1 mg to about 100 mg per kg of body weight per day, preferably from about 0.5 mg to about 25 mg per kg of body weight per day. The compounds of formula I are preferably administered orally but parenteral routes such as subcutaneous, intramuscular and intravenous can also be employed, as can topical routes of administration. The daily dose can be administered singly or it can be divided into two to four doses administered throughout the day.

The inhibitors of formula I can be administered in combination with human ANF (atrial natriuretic factor) 99–126. Such combination would contain the inhibitor of formula I at from about 1 to about 100 mg per kg of body weight, and the human ANF 99–126 at from about 0.001 to about 0.1 mg per kg of body weight.

The inhibitors of formula I can be administered in combination with other classes of pharmaceutically active compounds. For example, they can be administered with a diuretic, a calcium channel blocker, a potassium channel activator, a cholesterol reducing agent, a β-blocker, an angiotensin II antagonist, etc.

The inhibitors of formula I or a pharmaceutically acceptable salt thereof and other pharmaceutically acceptable ingredients can be formulated for the above described pharmaceutical uses. Suitable compositions for oral administration include tablets, capsules and elixirs, and suitable compositions for parenteral administration include sterile solutions and suspensions. Suitable compositions for treating glaucoma also include topical compositions such as solutions, ointments, and solid inserts as described in U.S. Pat. No. 4,442,089. About 10 to 500 mg of active ingredient is compounded with physiologically acceptable vehicle, carrier, excipient, binder, preservative, stabilizer, flavoring, etc., in a unit dose form as called for by accepted pharmaceutical practice.

The following examples are illustrative of the invention. Temperatures are given in degrees centigrade. Thin layer chromatography (TLC) was performed in silica gel unless otherwise stated.

EXAMPLE 1

[3R-[3α,6α(S*),11bβ]]-2,3,5,6,7,11b-Hexahydro-6-[(2-mercapto-1-oxo-3-phenylpropyl)amino]-5-oxo-thiazolo[2,3-a][2]benzazepine-3-carboxylic acid

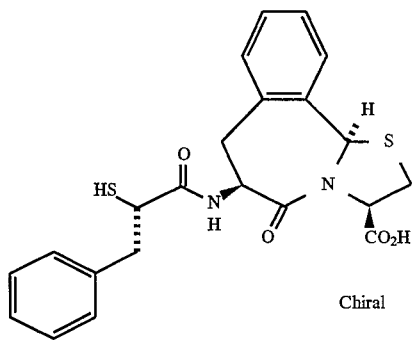

Chiral

A. 3-(Bromomethyl)benzenemethanol

To a solution of 1M boron tribromide in dichloromethane (49.2 mL, 49.2 mmol) cooled to 0° C. was added dropwise over 45 minutes a solution of 1,3-dihydroisobenzo-furan (17.40 g, 142.6 mmol) in dichloromethane (30 mL). After addition, the mixture was heated to reflux in an oil bath for 1 hour, then cooled down to room temperature and quenched with water (50 mL). The mixture was washed with water (100 mL), 50% saturated sodium bicarbonate (100 mL), water (100 mL) and brine, dried (magnesium sulfate) and concentrated in vacuo to give a brownish solid, which was crystallized from ethyl acetate/hexane to afford 16.442 g of compound A as a light yellow crystalline compound. The mother liquor was concentrated and the residue crystallized (ethyl acetate/hexane) to yield an additional 6.30 g of compound A (total amount of compound A, 22.742 g, 80% yield).

B. 1-(Bromomethyl)-2-[[[(1,1-dimethylethyl)dimethylsilyl]oxy]methyl]benzene

To a solution of compound A (10 g, 50 mmol) in dichloromethane (80 mL) cooled to 0° C. was added 2,6-lutidine (7.57 mL, 65 mmol), followed by dropwise addition of tert-butyldimethylsilyl trifluoromethanesulfonate (14.92 mL, 65 mmol). The reaction mixture was stirred at 0° C. for 45 minutes, then quenched with water (20 mL) and partitioned between ethyl acetate (450 mL) and water (150 mL). The organic layer was separated and washed with 10% sodium bicarbonate solution and brine (twice), dried (magnesium sulfate) and concentrated in vacuo to give a yellow syrup, which was chromatographed on a silica gel column eluting with 10–50% ethyl acetate/hexane to afford 13.89 g (88%) of compound B as a light yellow oil.

C. [3aS-(3aα,6α,7aβ)]-1-[[[Bis(methylthio)methylene]amino]acetyl]hexahydro-8,8-dimethyl-3H-3a,6-methano-2,1-benzisothiazole, 2,2-dioxide To a solution of [3aS-(3aα,6α,7aβ)]-hexahydro-8,8-dimethyl-3H-3a,6-methano-2,1-benzoisothiazole, 2,2-dioxide (8.40 g, 39 mmol) in toluene (210 mL) was added dropwise 2.0M trimethylaluminum solution in toluene (23.4 mL, 46.8 mmol). After addition, the mixture was stirred at room temperature for 15 minutes, and then a solution of N-[bis(methylthio)methylene]glycine methyl ester (10.556 g, 54.615 mmol) in 115 mL of toluene was added dropwise. After addition, the mixture was stirred at 50° C. under argon for 24 hours, and then cooled down to room temperature. Water (13.6 mL) was added dropwise to the stirring mixture over 2 hours (with caution) to decompose the remaining trimethylaluminum, followed by addition of magnesium sulfate. After stirring for 30 minutes, the mixture was filtered and the filtrate was concentrated in vacuo to give a yellow syrup which was chromatographed on a silica gel column using ethyl acetate/hexane (1:4) as a mobile phase to afford 12.787 g (87% yield) of compound C as a white solid.

D. [3aS-[1(R*),3aα,6α,7aβ]]-1-[2-[[Bis(methylthio)methylene]amino]-3-[2-[[[(1,1-dimethylethyl)dimethylsilyl]oxy]methyl]phenyl]-1-oxopropyl]hexahydro-8,8-dimethyl-3H-3a,6-methano-2,1-benzisothiazole, 2,2-dioxide To a solution of dry tetrahydrofuran (60 mL) cooled to −78° C. was added dropwise over 30 minutes a solution of 2.5M n-butyl lithium in hexane (12.10 mL, 30.24 mmol). After addition, compound C (11.385 g, 30.234 mmol) in 50 mL of tetrahydrofuran was added dropwise over 30 minutes via a dropping funnel. The resulting yellow mixture was stirred at −78° C. for 1 hour, and then compound B (11.44 g, 36.28 mmol) in 15 mL of tetrahydrofuran and 15 mL of hexamethyl phosphoric triamide was added over 20 minutes (the temperature of the reaction mixture was maintained at <−70° C.), followed by addition of n-tetrabutylammonium iodide (600 mg) in one portion. After addition, the temperature of the reaction mixture was warmed up from −70° C. to −40° C. over one hour, and from −40° C. to 0° C. over another hour. The reaction was quenched with water (100 mL) at 0° C., and partitioned between ethyl acetate (1 L) and water (300 mL). The organic phase was separated and washed with water and brine, dried (sodium sulfate), and concentrated in vacuo to give a yellowish syrup which was chromatographed on a silica gel column eluting with ethyl acetate/hexane (10–25%) to afford 17.40 g (95% yield) of compound D as a light yellow foam (d.e.>99% by HPLC).

E. [3aS-[1(R*),3aα,6α,7aβ]]-1-[2-Amino-3-[2-(hydroxymethyl)phenyl]-1-oxopropyl]hexahydro-8,8-dimethyl-3H-3a,6-methano-2,1-benzisothiazole, 2,2-dioxide To Compound D (6.09 g, 10 mmol) in a mixed solvent of tetrahydrofuran (36 mL) and ethylene glycol dimethyl ether (12 mL) cooled to 0° C. was added 1N aqueous hydrochloric acid (30 mL) and water (15 mL). The bi-phase mixture was stirred at room temperature under argon for 24 hours. The resulting homogeneous solution was concentrated in vacuo to remove most of the tetrahydrofuran and ethylene glycol dimethyl ether. The remaining aqueous mixture was cooled to 0° C., adjusted to pH 7 with 10N sodium hydroxide and extracted with ethyl acetate (4×120 mL). The combined ethyl acetate was washed with water and brine, dried (magnesium sulfate) and concentrated in vacuo to give compound E as a light yellow foam which was used in the next reaction without further purification.

F. (S)-α-Amino-2-(hydroxymethyl)benzenepropanoic acid

To a solution of compound E (ca. 10 mmol) in tetrahydrofuran (54 mL) was added aqueous lithium hydroxide (169 g of lithium hydroxide monohydrate in 27 mL of water). The mixture was stirred at room temperature under argon for 24 hours, diluted with 50 mL of water and extracted with dichloromethane (4×100 mL). The aqueous phase was adjusted to pH 5.35 with 6N hydrochloric acid and concentrated in vacuo to remove most of the water. The remaining approximately 30 mL of aqueous phase was lypholized to afford 4.01 g of light yellow solid which contained compound F and the lithium chloride salt. The crude product was used for the next reaction without further purification.

A sample of the pure product was obtained by purification on a CHP-20 column as a white powder.

[α]$^{rt}$D −30.5° (c 0.57, methanol)

$^1$H NMR (D$_2$O, 270 MHz): δ 3.05 (dd, J=8.8, 14.6 Hz, 1H), 3.11 (dd, J=4.0, 14.6 Hz, 1H), 3.90 (m, 1H), 4.65 (s, 2H), 7.20–7.40 (m, 5H).

$^{13}$C NMR (D$_2$O, 67.7 MHz): δ 34.98, 57.51, 63.45, 129.87, 130.74, 131.81, 132.38, 135.96, 140.26, 175.94

Mass Spec. (FAB): [M+H]$^+$ @196, MW=195

IR (KBr): 3422, 3063, 1632, 1495, 1402, 1337, 1009, 762 cm$^{-1}$

Analysis for C$_{10}$H$_{13}$NO$_3$•0.35 H$_2$O: Calculated: C, 59.63; H, 6.85; N, 6.95; Found: C, 59.72; H, 6.68; N, 6.86.

G. (S)-α-(1,3-Dihydro-1,3-dioxo-2H-isoindol-2-yl)-2-(hydroxymethyl)benzenepropanoic acid To a solution of crude compound F (ca. 10 mmol) in 15 mL of water was added sodium bicarbonate (1.68 g, 20 mmol), followed by 1,3-Dihydro-1,3-dioxo-2H-isoindole-2-carboxylic acid, ethyl ester (2.192 g, 10 mmol). The resulting suspension was stirred at room temperature for 2 hours. (It became almost homogeneous after 1 hour.) The mixture was filtered and the filtrate was extracted with ethyl acetate (2×100 mL). The aqueous phase was acidified to pH 2.75 with 6N hydrochloric acid and extracted with ethyl acetate (4×100 mL). The combined ethyl acetate extracts were washed with water and brine, dried (magnesium sulfate) and concentrated in vacuo. The crude product was chromatographed eluting with 0.5–2% acetic acid/ethyl acetate to afford 3.05 g of compound G as a white foam, which contained approximately 75% pure compound G determined by H$^1$-NMR.

H. (S)-α-(1,3-Dihydro-1,3-dioxo-2H-isoindol-2-yl)-2-formylbenzenepropanoic acid

To a solution of crude compound G (2.49 g) in dichloromethane (70 mL) was added manganese dioxide (7.5 g). The black suspension was stirred at room temperature for 6 hours and filtered via a pad of Celite®. The Celite® pad was washed with methanol/dichloromethane (20:80, 1 L) and acetic acid/methanol/dichloromethane (5:20:75, 2 L). The filtrate was concentrated and the residue was chromatographed on silica gel using 1–3% acetic acid/dichloromethane as a mobile phase to afford 1.312 g (50% yield from compound D over 4 steps) of pure compound H as an off-white solid.

I. (αS,4R)-α-(1,3-Dihydro-1,3-dioxo-2H-isoindol-2-yl)-2-[4-(methoxycarbonyl)-2-thiazolidinyl]benzenepropanoic acid To a solution of compound H (1.31 g) in 30 mL of dry tetrahydrofuran was added cysteine methyl ester hydrochloride (0.696 g, 4.056 mmol), followed by triethylamine (0.566 mL, 4.056 mmol). The resultant suspension was stirred at room temperature under argon for 4.5 hours and then concentrated in vacuo. The residue was partitioned between chloroform (120 mL) and water (30 mL). The organic phase was washed with water and the combined aqueous phases were back extracted with chloroform. The combined chloroform extracts were dried (sodium sulfate) and concentrated. The residue was evaporated with dichloromethane/toluene (twice) and dried in vacuo to yield compound I as a white foam which was used for the next reaction without further purification.

J. [3R-(3α,6α)]-6-(1,3-Dihydro-1,3-dioxo-2H-isoindol-2-yl)-2,3,5,6,7,11b-hexahydro-5-oxothiazolo[2,3-a][2]benzazepine-3-carboxylic acid, methyl ester To a solution of compound I in dry tetrahydrofuran (140 mL) was added 2-ethoxy-1-ethoxycarbonyl-1,2-dihydroquinoline (1.305 g, 5.273 mmol). The resultant solution was stirred at room temperature under argon for 3.5 days. After removal of tetrahydrofuran in vacuo, the remaining residue was taken into ethyl acetate (200 mL), washed with 5% potassium bisulfate, saturated sodium bisulfate, water and brine, dried (magnesium sulfate) and concentrated in vacuo. The residue was chromatographed on silica gel eluting with 20–30% ethyl acetate/hexane to give 1.48 g of compound J (86% over 2 steps from compound H) as a diastereomeric mixture (approximately 1:7 by HPLC).

K. [3R-(3α,6α)]-6-Amino-2,3,5,6,7,11b-hexahydro-5-oxothiazolo[2,3-a][2]benzazepine-3-carboxylic acid, methyl ester To a suspension of compound J (1.39 g, 3.294 mmol) in methanol (20 mL) was added dropwise hydrazine monohydrate (0.323 mL, 6.58 mmol). After stirring for 10 minutes, 2 mL of dichloromethane was added to the suspension. The resulting solution was stirred at room temperature under argon for 26 hours. (It became a white suspension after stirring for 12 hours.) The suspension was treated with 0.5N hydrochloric acid (33 mL) and stirred at 0° C. for 4 hours before filtration. The filtrate (aqueous hydrochloric acid solution) was extracted with ethyl acetate (twice), and the combined ethyl acetate extracts were back extracted with 0.5N hydrochloric acid. The combined hydrochloric acid solutions were cooled to 0° C., adjusted to pH 9 with dropwise addition of 4N sodium hydroxide and extracted with dichloromethane (four times). The combined dichloromethane extracts were washed with water and brine, dried (magnesium sulfate) and concentrated in vacuo to dryness to give 0.92 g (95 %) of compound K as a yellow foam which was used for the following reaction without further purification.

L. (S)-2-(Acetylthio)benzenepropanoic acid

Sodium nitrite (10.3 g, 280 mmol) was added to a solution of D-phenylalanine (30.0 g, 181 mmol) and potassium bromide (73.5 g) in sulfuric acid (2.5N, 365 ml) over a period of one hour while maintaining the temperature of the reaction mixture at 0° C. The mixture was stirred for an additional hour at 0° C. and then for one hour at room temperature. The reaction solution was extracted with ether, the ether was back extracted with water, and the ether layer was dried over sodium sulfate. Ether was removed in vacuo, and distillation of the oily residue afforded 25.7 g of (R)-2-bromo-3-benzenepropanoic acid; b.p. 141° C. (0.55 mm of Hg); [α]$_D$=+14.5° (c=2.4, chloroform).

A mixture of thioacetic acid (7 ml, 97.9 mmol) and potassium hydroxide (5.48 g, 97.9 mmol) in acetonitrile (180.5 ml) was stirred under argon at room temperature for 1¾ hours. The mixture was cooled in an ice-bath, and a solution of (R)-2-bromo-3-benzenepropanoic acid (20.4 g, 89 mmol) in acetonitrile (20 ml) was added over a ten minute period. The reaction was stirred under argon at room temperature for 5 hours and filtered, and the acetonitrile was removed in vacuo. The oily residue was dissolved in ethyl acetate and washed with 10% potassium bisulfate and water. Removal of the ethyl acetate in vacuo afforded 19.6 g of crude product. The crude product was purified via its dicyclohexylamine salt using isopropyl ether as solvent for crystallization. An analytical sample of (S)-2-(acetylthio) benzenepropanoic acid, dicyclohexylamine salt was prepared by recrystallization from ethyl acetate; m.p. 146°–147° C.; [α]$_D$=39.6° (c=1.39, chloroform).

Analysis calculated for C$_{11}$H$_{12}$O$_3$S•C$_{12}$H$_{23}$N: C, 68.11; H, 8.70; N, 3.45; S, 7.91 Found: C, 67.93; H, 8.71; N, 3.37; S, 7.94.

M. [3R-[3α,6α(S*),11bβ]]-6-[[2-(Acetylthio)-1-oxo-3-phenylpropyl]amino]-2,3,5,6,7,11b-hexahydro-5-oxothiazolo[2,3-a][2]benzazepine-3-carboxylic acid, methyl ester To a solution of compound L (840 mg) and compound K (920 mg, 3.147 mmol) in dichloromethane (25 mL) cooled to 0° C. was added triethylamine (517 µL, 3.713 mmol), followed by the addition of benzotriazol-1-yloxytris (dimethylamino)phosphonium hexafluorophosphate (1.642 g). The mixture was stirred at 0° C. for 1 hour, then at room temperature for 2.5 hours. The volatiles were removed in vacuo. The residue was taken into ethyl acetate (250 mL), washed with 5% potassium bisulfate, water, saturated sodium bicarbonate, water and brine, dried (sodium sulfate), filtered and evaporated to dryness to give a diastereomeric mixture. The crude product was flash chromatographed on silica gel eluting with 20–40% ethyl acetate/hexane to give 155.4 mg (10%) of compound L as a white foam and 976 mg (62%) of [3R-[3α,6α(S*),11bα]]-6-[[2-(acetylthio)-1-oxo-3-phenylpropyl]amino]-2,3,5,6,7,11b-hexahydro-5-oxo-thiazolo[2,3-a][2]benzazepine-3-carboxylic acid, methyl ester as a white foam.

N. [3R-[3α,6α(S*),11bβ]]-2,3,5,6,7,11b-Hexahydro-6-[(2-mercapto-1-oxo-3-phenylpropyl)amino]-5-oxo-thiazolo[2,3-a][2]benzazepine-3-carboxylic acid A solution of compound M (131 mg, 0.263 mmol) in tetrahydrofuran (1.6 mL), ethylene glycol dimethyl ether (0.5 mL) and water (0.8 mL) cooled to 0° C. was purged with argon for 1 hour, then treated portionwise with lithium hydroxide monohydrate (44 mg). The resulting yellow solution was stirred at 0° C., while maintaining the bubbling of argon, for 2 hours, then acidified with 1M potassium bisulfate to pH 1–2, and extracted with ethyl acetate (three times). The combined ethyl acetate extracts were washed with brine (twice), dried (sodium sulfate), filtered and evaporated to dryness. The residue was flash chromatographed on silica gel using 0.3–0.5% acetic acid/ethyl acetate as a mobile phase to give 77 mg (58%) of the title compound as a white foam.

TLC: Rf=0.34, 1% acetic acid/ethyl acetate (UV and PMA detection), silica gel.

[α]$^{rt}_D$=+12.2° (c 0.5, methanol).

$^1$H NMR (CDCl$_3$; 400 MHz): δ 2.03 (d, J=8.5 Hz, 1H), 2.95–3.17 (m, 3H), 3.20–3.40 (m, 3H), 3.58 (m, 1H), 4.93 (m, 1H), 5.30 (m, 1H); 6.45 (s, 1H), 7.08 (d, J=5.5 Hz, 1H), 7.15–7.35 (m, 7H), 7.47 (d, J=5.5 Hz, 1H), 7.65 (d, J=8.5 Hz, 1H).

$^{13}$C NMR (CDCl$_3$; 100 MHz): δ 31.89, 36.69, 41.35, 44.33, 49.83, 63.31, 65.20, 126.53, 126.64, 127.02, 128.48, 129.07, 129.42, 131.14, 133.58, 135.28, 137.47, 169.64, 171.58, 172.08.

Mass Spec. [M+H]$^+$ (high resolution FAB): calculated for C$_{22}$H$_{22}$N$_2$O$_4$S$_2$: 443.1099; Found: 443.1083 (deviation 3.6 ppm).

IR (KBr): 3422, 3061, 3028, 2928, 2558, 1736, 1651, 1520, 1497, 1445, 1200, 756, 700 cm$^{-1}$.

Elemental Microanalysis for C$_{22}$H$_{22}$N$_2$O$_4$S$_2$: Calculated: C, 59.71; H, 5.01; N, 6.33; Found: C, 59.66; H, 5.09; N, 6.47.

EXAMPLE 2

[3R-[3α,6α(S*),11bβ]]-2,3,5,6,7,11b-Hexahydro-6-[(2-mercapto-1-oxo-3-phenylpropyl)amino]-5-oxo-thiazolo[2,3-a][2]benzazepine-3-carboxylic acid

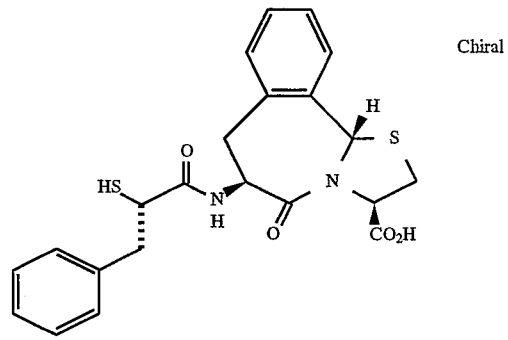

A. [3R-[3α,6α(S*),11bβ]]-2,3,5,6,7,11b-Hexahydro-6-[(2-mercapto-1-oxo-3-phenylpropyl)amino]-5-oxo-thiazolo-[2,3-a][2]benzazepine-3-carboxylic acid A solution of [3R-[3α,6α(S*),11bβ]]-6-[[2-(acetylthio)-1-oxo-3-phenylpropyl]amino]-2,3,5,6,7,11b-hexahydro-5-oxo-thiazolo[2,3-a][2]benzazepine-3-carboxylic acid, methyl ester (599 mg, 1.203 mmol, prepared as described in Example 1, above) in tetrahydrofuran (7.0 mL) cooled to 0° C. was purged with argon for 30 minutes, then treated dropwise with a previously purged aqueous lithium hydroxide solution (202 mg of lithium hydroxide in 3.5 mL of water). The resulting turbid solution was stirred at 0° C., while maintaining the bubbling of argon, for 2.5 hours. (It became clear after 1 hour stirring.) Then, the compound was acidified with 1M potassium bisulfate to pH 2 and extracted with ethyl acetate (three times). The combined ethyl acetate extracts were washed with 50% saturated brine and brine, dried (sodium sulfate), filtered and evaporated to dryness. The residue was purified by preparative HPLC using 0.1% trifluoroacetic acid in acetonitrile/water (45:55) as a mobile phase to give 332.6 mg (62%) of the title compound as a white powder.

TLC: Rf=0.41, 3% acetic acid/ethyl acetate (UV and PMA detection), silica gel.

[α]$^{rt}_D$=−7.9° (c 0.6, methanol).

$^1$H NMR (CDCl$_3$; 300 MHz): δ 2.13 (d, J=9.0 Hz, 1H), 2.80–3.70 (m, 7H), 4.10 (m, 1H), 5.20 (d, J=5.4 Hz, 1H), 6.60 (s, 1H), 7.20–7.40 (m, 8H), 7.73 (d, J=6.4 Hz, 1H), 7.84 (m, 1H).

$^{13}$C NMR (CDCl$_3$; 100 MHz): δ 30.47, 34.41, 41.47, 43.97, 55.05, 61.54, 66.21, 124.92, 126.90, 127.81, 128.43, 128.74, 129.34, 129.44, 129.91, 135.56, 137.63, 169.94, 171.42, 173.26.

Mass Spec. [M+H]$^+$ (relative intensity): 443 (100).

IR (KBr): 3368, 3063, 3030, 2932, 1742, 1642, 1524, 1400, 1339, 1171, 752, 700 cm$^{-1}$.

Elemental Microanalysis for C$_{22}$H$_{22}$N$_2$O$_4$S$_2$·0.40 H$_2$O·0.07 C$_7$H$_{16}$: Calculated: C, 59.14; H, 5.28; N, 6.13; S, 14.04; Found: C, 59.16; H, 5.11; N, 5.96; S, 13.62.

What is claimed is:
1. A compound of the formula

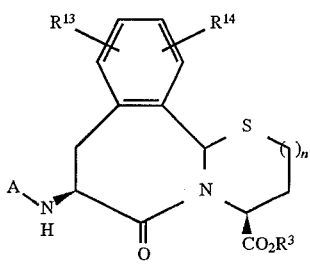

and pharmaceutically acceptable salts thereof wherein:

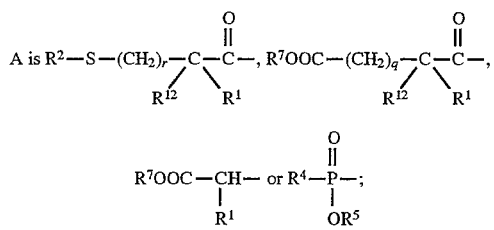

$R^1$ and $R^{12}$ are independently selected from hydrogen, alkyl, alkenyl, cycloalkyl, substituted alkyl, substituted alkenyl, aryl, substituted aryl, heteroaryl, cycloalkyl-alkylene-, aryl-alkylene-, substituted aryl-alkylene- and heteroaryl-alkylene-, or $R^1$ and $R^{12}$ taken together with the carbon atom to which they are attached, complete a cycloalkyl ring or a benzofused cycloalkyl ring;

$R^2$ is hydrogen,

or $R^{11}$—S—;

$R^3$, $R^5$ and $R^7$ are independently selected from hydrogen, alkyl, substituted alkyl, aryl-$(CH_2)_p$—, substituted aryl-$(CH_2)_p$—, heteroaryl-$(CH_2)_p$—,

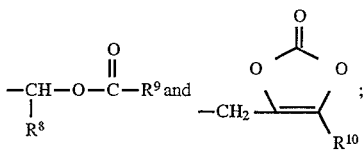

$R^4$ is alkyl, cycloalkyl-$(CH_2)_p$—, substituted alkyl, aryl-$(CH_2)_p$—, substituted aryl-$(CH_2)_p$— or heteroaryl-$(CH_2)_p$—;

$R^6$ is alkyl, substituted alkyl, cycloalkyl-$(CH_2)_p$—, aryl-$(CH_2)_p$—, substituted aryl-$(CH_2)_p$— or heteroaryl-$(CH_2)_p$—;

$R^8$ is hydrogen, lower alkyl, cycloalkyl or phenyl;

$R^9$ is hydrogen, lower alkyl, lower alkoxy or phenyl;

$R^{10}$ is lower alkyl or aryl-$(CH_2)_p$—;

$R^{11}$ is hydrogen, alkyl, substituted alkyl, cycloalkyl-$(CH_2)_p$—, aryl-$(CH_2)_p$—, substituted aryl-$(CH_2)_p$— or heteroaryl-$(CH_2)_p$—, or —S—$R^{11}$ completes a symmetrical disulfide wherein $R^{11}$ is

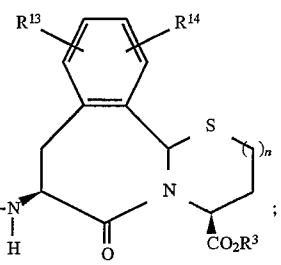

$R^{13}$ and $R^{14}$ are each independently selected from hydrogen, alkyl, substituted alkyl, aryl, substituted aryl, halogen, alkoxy and aryl-alkylene-, or $R^{13}$ and $R^{14}$ taken together with the carbon atoms to which they are attached complete a six-membered aromatic ring;

n is zero or one;

p is zero or an integer from 1 to 6;

q is zero or an integer from 1 to 3;

r is zero or one;

the term "alkyl" refers to straight or branched chain radicals of one to seven carbon atoms;

the term "alkoxy" refers to such alkyl groups as defined above attached to an oxygen;

the term "lower alkyl" refers to straight or branched chain radicals of one to four carbon atoms;

the term "substituted alkyl" refers to such straight or branched chain radicals of one to seven carbons wherein one or more hydrogens have been replaced by a hydroxy, amino, cyano, halo, trifluoromethyl, —NH(lower alkyl), —N(lower alkyl)$_2$, lower alkoxy, lower alkylthio, or carboxy;

the terms "lower alkoxy" and "lower alkylthio" refer to such lower alkyl groups as defined above attached to oxygen or sulfur atom, respectively;

the term "cycloalkyl" refers to saturated rings of 3 to 7 carbon atoms;

the term "alkenyl" refers to straight or branched chain radicals of 3 to 7 carbon atoms having one two double bonds;

the term "substituted alkenyl" refers to such straight or branched chain radicals of 3 to 7 carbon atoms having one or two double bonds wherein a hydrogen has been replaced by hydroxy, amino, halo, trifluoromethyl, cyano, —NH(lower alkyl), —N(lower alkyl)$_2$, lower alkoxy, lower alkylthio, or carboxy;

the term "alkylene" refers to straight or branched chain radicals having one to seven carbon atoms;

the term "aryl" refers to phenyl, 1-naphthyl, and 2-naphthyl;

the term "substituted aryl" refers to phenyl, 1-naphthyl, and 2-naphthyl having a substituent selected from lower alkyl, lower alkoxy, lower alkylthio, halo, hydroxy, trifluoromethyl, amino, —NH(lower alkyl), —N(lower alkyl)$_2$, and di and tri-substituted phenyl, 1-naphthyl, and 2-naphthyl wherein said substituents are selected from methyl, methoxy, methylthio, halo, hydroxy, and amino;

the term "heteroaryl" refers to 2-pyridyl, 3-pyridyl, 4-pyridyl, 4-imidazolyl, 4-thiazolyl, 2-thienyl, 3-thienyl, 2-furyl, 3-furyl, 2-indolyl, 3-indolyl, 4-quinolinyl, and 5-quinolinyl; and the term "halo" refers to chloro, bromo, fluoro and iodo.

2. A compound of claim 1, wherein A is $$R^2-S-(CH_2)_r-\underset{R^{12}}{\underset{|}{C}}-\overset{O}{\overset{\|}{C}}-.$$

3. A compound of claim 1, wherein A is $$R^7OOC-(CH_2)_q-\underset{R^{12}}{\underset{|}{C}}-\overset{O}{\overset{\|}{C}}-.$$

4. A compound of claim 1, wherein A is $$R^7OOC-\underset{R^1}{\underset{|}{C}H}-.$$

5. A compound of claim 1, wherein A is $$R^4-\overset{O}{\overset{\|}{\underset{OR^5}{\underset{|}{P}}}}-.$$

6. A compound of claim 1, wherein $R^{13}$ and $R^{14}$ are each independently selected from hydrogen, alkyl, substituted alkyl, aryl, substituted aryl, halogen, alkoxy and arylalkylene-.

7. A compound of claim 1, wherein $R^{13}$ and $R^{14}$, taken together with the carbon atoms to which they are attached, complete a six-membered aromatic ring.

8. A compound of claim 1, wherein A is $$R^2-S-(CH_2)_r-\underset{R^{12}}{\underset{|}{C}}-\overset{O}{\overset{\|}{C}}-$$

and n is zero.

9. A compound of claim 1, wherein A is $$R^2-S-(CH_2)_r-\underset{R^{12}}{\underset{|}{C}}-\overset{O}{\overset{\|}{C}}-;$$

$R^1$, $R^2$, $R^3$, $R^{13}$ and $R^{14}$ are each hydrogen;
$R^{12}$ is benzyl;
n is zero; and
r is zero.

10. A compound of claim 1, selected from the group consisting of:
[3R-[3α,6α(S*),11bβ]]-2,3,5,6,7,11b-Hexahydro-6-[(2-mercapto-1-oxo-3-phenylpropyl)amino]-5-oxo-thiazolo[2,3-a][2]benzazepine-3-carboxylic acid, and
[3R-[3α,6α(S*),11bβ]]-2,3,5,6,7,11b-Hexahydro-6-[(2-mercapto-1-oxo-3-phenylpropyl)amino]-5-oxo-thiazolo[2,3-a][2]benzazepine-3-carboxylic acid.

11. A pharmaceutical composition useful in the treatment of cardiovascular diseases comprising a pharmaceutically acceptable carrier and a cardiovascularly effective amount of at least one compound of the formula or a pharmaceutically acceptable salt thereof wherein:

A, n, $R^3$, $R^{13}$ and $R^{14}$ are as defined in claim 1.

12. A method of treating cardiovascular diseases in a mammal which comprises administering to said mammal an effective amount of the composition of claim 11.

13. A compound of the formula wherein:

$R^3$ is alkyl, substituted alkyl, aryl-$(CH_2)_p$—, or substituted aryl-$(CH_2)_p$—;

$R^{13}$ and $R^{14}$ are each independently selected from hydrogen, alkyl, substituted alkyl, aryl, substituted aryl, halogen, alkoxy, aryl-alkylene, or $R^{13}$ and $R^{14}$ taken together with the carbon atoms to which they are attached complete a six-membered aromatic ring;

p is zero or an integer from 1 to 6;

n is zero or one;

the term "alkyl" refers to straight or branched chain radicals of one to seven carbon atoms;

the terms "alkoxy" refers to such alkyl groups as defined above attached to an oxygen atom;

the term "substituted alkyl" refers to such straight or branched chain radicals of one to seven carbons wherein one or more hydrogens have been replaced by a hydroxy, amino, cyano, halo, trifluoromethyl, —NH(lower alkyl), —N(lower alkyl)$_2$, lower alkoxy, lower alkylthio, or carboxy;

the term "lower alkyl" refer to straight or branched chain radicals of one to four carbon atoms;

the terms "lower alkoxy" and "lower alkylthio" refer to such lower alkyl groups as defined above attached to an oxygen or sulfur atom, respectively;

the term "alkylene" refers to straight or branched chain radicals having one to seven carbons;

the term "aryl" refers to phenyl, 1-naphthyl, and 2-naphthyl;

the term "substituted aryl" refers to phenyl, 1-naphthyl, and 2-naphthyl having a substituent selected from lower alkyl, lower alkoxy, lower alkylthio, halo, hydroxy, trifluoromethyl, amino, —NH(lower alkyl), —N(lower alkyl)$_2$, and di and tri-substituted phenyl, 1-naphthyl, and 2-naphthyl wherein said substituents are selected from methyl, methoxy, methylthio, halo, hydroxy, and amino; and the term "halo" refers to chloro, bromo, fluoro, and iodo.

14. A compound of claim 13 wherein:
$R^{13}$ and $R^{14}$ are both hydrogen;
n is zero; and
$R^3$ is methyl.

* * * * *